US009500663B2

(12) United States Patent
Tieman et al.

(10) Patent No.: US 9,500,663 B2
(45) Date of Patent: Nov. 22, 2016

(54) REDUNDANT IDENTIFICATION FOR SAMPLE TRACKING ON A DIAGNOSTIC DEVICE

(71) Applicant: GENMARK DIAGNOSTICS, INC., Carlsbad, CA (US)

(72) Inventors: Brad Frederick Tieman, Encinitas, CA (US); Scott Corey, Hydes, MD (US)

(73) Assignee: GENMARK DIAGNOSTICS, INC., Carlsbad, CA (US)

( * ) Notice: Subject to any disclaimer, the term of this patent is extended or adjusted under 35 U.S.C. 154(b) by 0 days.

(21) Appl. No.: 14/538,602

(22) Filed: Nov. 11, 2014

(65) Prior Publication Data

US 2016/0131672 A1    May 12, 2016

(51) Int. Cl.
*G01N 35/00* (2006.01)
*B01L 3/00* (2006.01)

(52) U.S. Cl.
CPC ......... *G01N 35/00732* (2013.01); *B01L 3/545* (2013.01); *B01L 2300/021* (2013.01); *G01N 2035/00752* (2013.01); *G01N 2035/00762* (2013.01); *G01N 2035/00772* (2013.01); *G01N 2035/00782* (2013.01); *G01N 2035/00801* (2013.01); *G01N 2035/00831* (2013.01); *G01N 2035/00851* (2013.01)

(58) Field of Classification Search
CPC ............. G01N 35/00732; G01N 2035/00742; G01N 2035/00752; G01N 2035/00762; G01N 2035/00772; G01N 2035/00782; G01N 2035/00792; B01L 3/54
See application file for complete search history.

(56) References Cited

U.S. PATENT DOCUMENTS

| 4,678,894 | A | 7/1987 | Shafer |
|---|---|---|---|
| 6,599,476 | B1 | 7/2003 | Watson et al. |
| 6,830,181 | B1 | 12/2004 | Bennett |
| 6,983,884 | B2 | 1/2006 | Auchinleck |
| 7,187,286 | B2 | 3/2007 | Morris et al. |
| 7,284,704 | B2 | 10/2007 | Lubow |
| 7,487,914 | B2 | 2/2009 | Yoon et al. |
| 7,490,766 | B2 | 2/2009 | Auchinleck |
| 7,490,767 | B2 | 2/2009 | Auchinleck |
| 8,261,981 | B2 | 9/2012 | Auchinleck |
| 8,281,997 | B2 | 10/2012 | Moran et al. |
| 8,292,178 | B2 | 10/2012 | Chaves |
| 2004/0228765 | A1 | 11/2004 | Witty et al. |

(Continued)

FOREIGN PATENT DOCUMENTS

WO    WO2014066704 A1    5/2014

OTHER PUBLICATIONS

International Search Report and Written Opinion issued by the European Patent Office in International Patent Application No. PCT/US2015/059938, 14 pages (Feb. 19, 2016).

*Primary Examiner* — Paul Hyun
(74) *Attorney, Agent, or Firm* — Rothwell, Figg, Ernst & Manbeck PC

(57) ABSTRACT

A sample-containing device configured to be placed into a sample processing instrument for performing a process on a sample contained in the device includes redundant identification features, such as machine-readable tags. A first machine-readable information tag is read before the device is placed in the instrument, and a second machine-readable information tag is read after the device is in the instrument. Information read from the two tags is compared to determine if there is proper correspondence between the information read from the tags to ensure that the correct sample processing device was placed in the instrument.

10 Claims, 4 Drawing Sheets

(56) References Cited

U.S. PATENT DOCUMENTS

| | | |
|---|---|---|
| 2004/0228766 A1 | 11/2004 | Witty et al. |
| 2006/0153736 A1 | 7/2006 | Kalra et al. |
| 2009/0218401 A1 | 9/2009 | Moran et al. |
| 2011/0079641 A1 | 4/2011 | Cantor |
| 2012/0297255 A1 | 11/2012 | Case et al. |
| 2014/0194305 A1 | 7/2014 | Kayyem et al. |
| 2014/0322706 A1 | 10/2014 | Kayyem et al. |
| 2015/0323555 A1 | 11/2015 | Kayyem et al. |

REDUNDANT IDENTIFICATION FOR SAMPLE TRACKING ON A DIAGNOSTIC DEVICE

FIELD OF THE DISCLOSURE

This disclosure describes methods, systems, and apparatus for providing redundant identification of a sample device to ensure accurate identification of the sample contained in the sample device.

BACKGROUND

Instruments or systems for performing diagnostic tests or other processes on patient samples, such as molecular diagnostic tests, commonly employ barcode technology to encode a patient or sample ID (also called an accession ID) to track a sample throughout a laboratory facility. A barcode is placed on a device associated with the sample, such as a test tube, cuvette, bottle or other container, a slide, a multi-chamber integrated test cartridge, or other device. In some cases the device is disposable and is discarded after the test procedure is complete and the results are recorded. The barcode is manually scanned or is read by a fixed scanner on the instrument before or after the device is placed into the instrument, thereby providing an association between the information encoded in the barcode and the contents of the device. For obvious reasons, it is critical that the association between the information encoded in the barcode and the contents of the device be accurate. That is, if the device contains a patient sample, it is critical that the information encoded in the barcode on that device identify the correct patient.

When a barcode, or other scannable ID tag, is scanned outside an instrument before placing the device in the instrument, the association between the contents of the device and the information encoded in a barcode is created outside the instrument, and that association may apply throughout the processing operation. For example, when an instrument has a number of distinct processing locations in which a device may be placed for processing, the user may select an available processing location or the instrument may instruct the user which processing location to use next. In this case, the association between the ID information and the device contents for a particular processing location is created before the device is placed in that processing location. For example, if the use selects or is instructed to next load processing location "six" and then scan an ID for "patient B", the instrument will be expecting patient B's sample in processing location six, and the results of the test that is performed in processing location six will be associated with patient B. Thus, a problem is created if, after creating the association between processing location six and patient B, a device containing another patient's sample, "patient C," is placed in processing location six.

Often when a diagnostic instrument is being prepared for operation by laboratory personnel, there are multiple sample devices that must be loaded into the instrument, each device with its own unique accession ID or barcode. If the laboratory personnel scans the ID code of a first device, i.e., "device A," and then mistakenly loads a different device, i.e., "device B," into the instrument, the instrument will incorrectly associate the results of tests performed on patient B's sample to patient A.

SUMMARY

This disclosure describes methods, systems, and apparatus for providing redundant identification of the sample device—both inside and outside an instrument—to ensure accurate identification of the sample contained in the sample device.

According to one aspect of the disclosure a sample processing cartridge comprises a substrate configured to be inserted into a sample processing instrument, a sample compartment supported on the substrate and configured to contain a sample material, and one or more process compartments supported on the substrate and configured to contain a process material. The sample compartment is connected or connectable to at least one process compartment. The cartridge includes first machine-readable information tag mounted on or embedded in the substrate, encoded with cartridge-identifying information, and configured to be read by a device that is external to a sample processing instrument. The cartridge also includes a second machine-readable information tag mounted on or embedded in the substrate, encoded with cartridge-identifying information corresponding to the cartridge-identifying information encoded in the first machine-readable information tag, and configured to be read by a device within a sample processing instrument.

According to another aspect of the disclosure, the first machine-readable information tag comprises an optically-readable tag.

According to another aspect of the disclosure, the first machine-readable information tag comprises a bar code.

According to another aspect of the disclosure, the first machine readable information tag comprises a 1-D or a 2-D bar code.

According to another aspect of the disclosure, the second machine-readable information tag comprises an electronically-readable tag.

According to another aspect of the disclosure, the second machine-readable information tag comprises a wirelessly-readable tag.

According to another aspect of the disclosure, the second machine-readable information tag comprises an RFID tag or an EEPROM tag.

According to another aspect of the disclosure, the cartridge-identifying information encoded in the second machine-readable information tag comprises information that is identical to the cartridge-identifying information encoded in the first machine-readable information tag.

According to another aspect of the disclosure, the cartridge-identifying information comprises an identification code comprised of a unique combination of numeric and/or alphabetic characters.

According to another aspect of the disclosure, the cartridge further comprises a machine-readable sample identification tag encoded with sample-identifying information and configured to be read by a device that is external to a sample processing instrument.

Another aspect of the disclosure is embodied in a system for processing a sample. The system comprises a sample processing cartridge, which comprises a substrate, a sample compartment supported on the substrate and configured to contain a sample material, one or more process compartments supported on the substrate and configured to contain a process material. The sample compartment is connected or connectable to at least one process compartment. The cartridge further includes a first machine-readable information tag mounted on or embedded in the substrate and encoded with cartridge-identifying information and configured to be read by a device that is external to a sample processing instrument and a second machine-readable information tag mounted on or embedded in the substrate and encoded with cartridge-identifying information corresponding to the cartridge-identifying information encoded in the first machine-readable information tag. The system further includes a first tag reading device configured to read the first machine-readable information tag and to read a machine-readable sample identification tag placed on the cartridge and a first data processor element configured to associate information read from the first machine-readable information tag by the first tag reading device with information read from the machine-readable sample identification tag by the first tag reading device. The system further includes a processing instrument configured to receive the sample processing cartridge, a second tag reading device operatively associated with the processing instrument and configured to read the second machine-readable information tag when a sample processing cartridge is placed in the processing instrument, and a second data processor element configured to compare the information read from the second machine-readable information tag by the second tag reading device with information read from the first machine-readable information tag by the first tag reading device to ensure the cartridge-identifying information contained in the first machine-readable information tag corresponds to the cartridge-identifying information contained in the second machine-readable information tag.

According to another aspect of the disclosure, the second data processing element is further configured to enable operation of the processing instrument if the cartridge-identifying information contained in the first machine-readable information tag corresponds to the cartridge-identifying information contained in the second machine-readable information tag or disable operation of the processing instrument if the cartridge-identifying information contained in the first machine-readable information tag does not correspond to the cartridge-identifying information contained in the second machine-readable information tag.

According to another aspect of the disclosure, the first machine-readable information tag comprises an optically-readable tag, and the first tag reading device comprises an optical tag scanner.

According to another aspect of the disclosure, the first machine-readable information tag comprises a bar code, and the first tag reading device comprises a hand-held bar-code scanner.

According to another aspect of the disclosure, the first machine readable information tag comprises a 1-D or a 2-D bar code.

According to another aspect of the disclosure, the second machine-readable information tag comprises an electronically-readable tag, and the second tag reading device comprises an electronic tag reading device.

According to another aspect of the disclosure, the second machine-readable information tag comprises a wirelessly-readable tag, and the second tag reading device comprises a wireless tag scanner.

According to another aspect of the disclosure, the second machine-readable information tag comprises an RFID tag or an EEPROM tag.

According to another aspect of the disclosure, the cartridge-identifying information encoded in the second machine-readable information tag comprises information that is identical to the cartridge-identifying information encoded in the first machine-readable information tag.

According to another aspect of the disclosure, the cartridge-identifying information comprises an identification code comprised of a unique combination of numeric and/or alphabetic characters Other features and characteristics of the subject matter of this disclosure, as well as the methods of operation, functions of related elements of structure and the combination of parts, and economies of manufacture, will become more apparent upon consideration of the following description and the appended claims with reference to the accompanying drawings, all of which form a part of this specification, wherein like reference numerals designate corresponding parts in the various figures.

DETAILED DESCRIPTION

Figure 1:
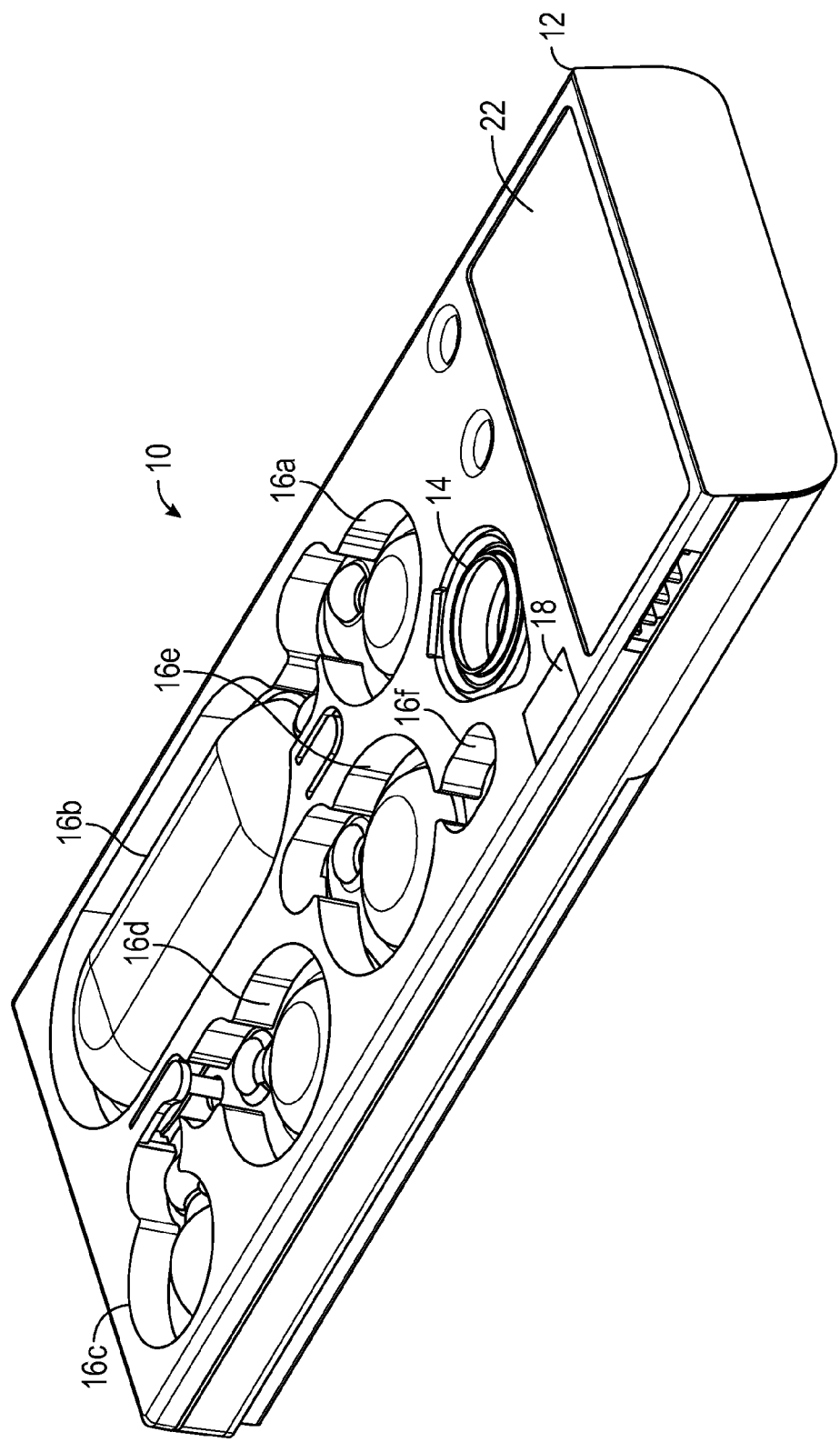
FIG. 1 is a perspective view of a sample processing cartridge including redundant cartridge identification features.

While aspects of the subject matter of the present disclosure may be embodied in a variety of forms, the following description and accompanying drawings are merely intended to disclose some of these forms as specific examples of the subject matter. Accordingly, the subject matter of this disclosure is not intended to be limited to the forms or embodiments so described and illustrated.

Unless defined otherwise, all terms of art, notations and other technical terms or terminology used herein have the same meaning as is commonly understood by one of ordinary skill in the art to which this disclosure belongs. All patents, applications, published applications and other publications referred to herein are incorporated by reference in their entirety. If a definition set forth in this section is contrary to or otherwise inconsistent with a definition set forth in the patents, applications, published applications, and other publications that are herein incorporated by reference, the definition set forth in this section prevails over the definition that is incorporated herein by reference.

Unless otherwise indicated or the context suggests otherwise, as used herein, "a" or "an" means "at least one" or "one or more."

This description may use relative spatial and/or orientation terms in describing the position and/or orientation of a component, apparatus, location, feature, or a portion thereof. Unless specifically stated, or otherwise dictated by the context of the description, such terms, including, without limitation, top, bottom, above, below, under, on top of, upper, lower, left of, right of, in front of, behind, next to, adjacent, between, horizontal, vertical, diagonal, longitudinal, transverse, radial, axial, etc., are used for convenience in referring to an absolute or relative position and/or orientation of such component, apparatus, location, feature, or a portion thereof in the drawings and are not intended to be limiting.

Furthermore, unless otherwise stated, any specific dimensions mentioned in this description are merely representative of an exemplary implementation of a device embodying aspects of the disclosure and are not intended to be limiting.

Figure 2:
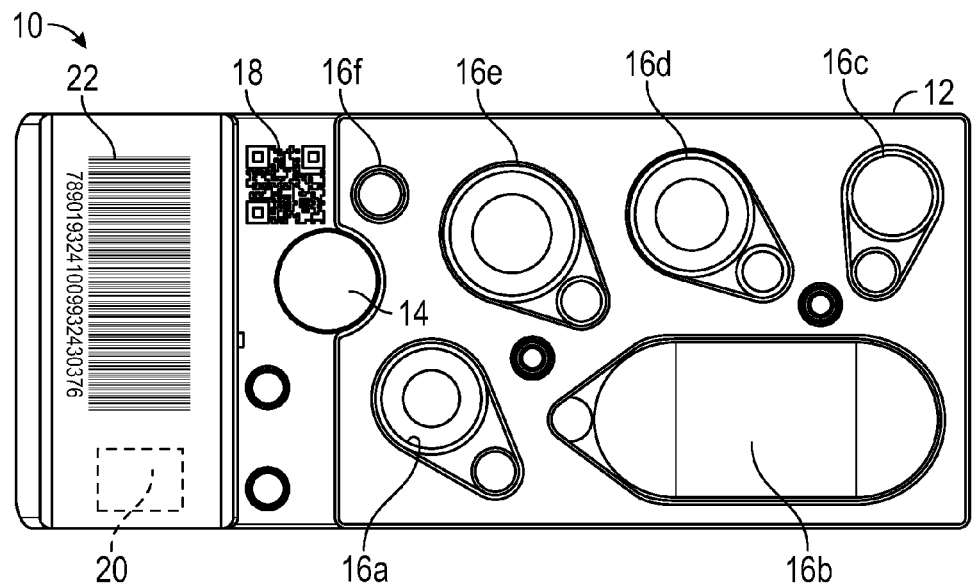
FIG. 2 is a top plan view of the cartridge.

A sample processing cartridge having redundant data features as disclosed herein is shown in FIGS. 1 and 2. The sample processing cartridge 10 includes a substrate 12 on which at least one sample compartment 14 and one or more process compartments 16a-16f are supported. The substrate may comprise any suitable structure, such as a panel, a shroud, a housing, or some combination thereof for supporting or mounting thereon or therein the sample compartment 14 and the one or more process compartments 16a-16f. In various embodiments, the substrate 12 is made of a lightweight, inexpensive material suitable for high-volume manufacturing, such as plastic.

The sample compartment 14 may comprise a well mounted on or formed within the substrate 12 and may further include a cap configured to be engaged with the well to selectively open or close the well. The sample compartments 16a-16f may comprise chambers or vessels suitable for containing therein a process material, or suitable for receiving a process material, that may be used in connection with an assay or other test procedure performed on a sample material with the cartridge. Exemplary process materials include reagents, buffers, oil, particles for immobilizing thereon analytes of interest within the sample, such as magnetic particles, etc. One or more of the process compartments 16a-16f may be initially empty and may be configured to receive a process material, a mixture of process materials from one or more of the other compartments, and/or a mixture of process material(s) and sample material, or the process compartment may be configured to receive waste material generated during a sample processing operation. The sample compartment 14 may be connected directly or indirectly to one or more of the process compartments 16a-16f and/or to inlet or outlet ports by channels or conduits which may be formed in the substrate 12. In addition, one or more of the process compartments 16a-16f may be connected directly or indirectly to each other and/or to inlet or outlet ports by channels or conduits formed in the substrate 12.

The process compartments 16a-16f may comprise deformable pouches or blisters configured to be collapsed upon application of an externally applied force to expel the contents of the compartment out of the compartment and into a conduit or other location within the cartridge 10. Alternatively, or in addition, the cartridge 10 may be configured to be coupled to an external source of positive or negative pressure for generating material motive forces for moving fluids or other materials into and/or out of the various compartments of the cartridge 10.

The sample processing cartridge 10 includes redundant identification features so that the cartridge may be first automatically identified using a first of the redundant identification features before the cartridge is placed into a processing instrument and then identified a second time using a second of the redundant identification features (i.e., a confirmatory identification) after the cartridge is placed into a processing instrument. Correspondence between the first and second identifications helps ensure that the cartridge identified outside of the processing instrument is the same cartridge later identified inside the processing instrument.

A first of the redundant identification features comprises a first machine-readable information tag 18. In the illustrated embodiment, the first machine-readable information tag 18 comprises an optically-readable tag, such as a one-dimensional barcode or a two-dimensional barcode (as shown) mounted on an external surface of the substrate 12. In an alternative embodiment, the first machine-readable information tag may comprise an electronically-readable tag and may comprise a device configured for wireless (or contactless) scanning, such as an RFID tag embedded within the substrate 12 and readable using a RFID tag reader or an electronically erasable programmable read-only memory module (EEPROM) mounted on or embedded within the substrate 12.

The first machine-readable information tag 18 may be encoded with cartridge-identifying information, which may comprise numeric and/or alphanumeric symbols, such as a serial number uniquely associated with that particular cartridge, and which can be accessed by a suitable tag reading device, such as a barcode reader, an RFID reader, or an EEPROM reader.

The second of the redundant identification features comprises a second machine-readable information tag 20. In the illustrated embodiment, the second machine-readable information tag is indicated by a dashed rectangle in FIG. 2 indicating a machine-readable tag that is embedded in the substrate 12. In various embodiments, the second machine-readable information tag comprises an electronically-readable tag or chip, such as an RFID chip or an EEPROM chip, embedded within the substrate 12. In other embodiments, the second machine-readable information tag 20 may comprise an optically-readable tag mounted on an exterior surface of the substrate 12, such as a one-dimensional or two-dimensional barcode.

The second machine readable information tag is encoded with information identifying the cartridge 10. In one embodiment, a serial number uniquely associated with the cartridge 10 may be encoded in the second machine-readable information tag 20, and that serial number will be accessible by an appropriate reading device such as an RFID reader, an EEPROM reader, or a barcode reader (scanner).

To provide the redundant identification, the cartridge identifying information encoded into the first machine-readable information tag preferably corresponds to the cartridge identifying information encoded into the second machine-readable information tag. The correspondence between the cartridge identifying information encoded into the first machine-readable information tag and the cartridge identifying information encoded into the second machine-readable information tag creates a one-to-one association between the cartridge identifying information in each tag. In one embodiment, the correspondence between the cartridge identifying information encoded into the first and second machine-readable information tags is provided by using identical cartridge identifying information in each tag, such as an identical serial number uniquely associated with the cartridge 10. In an alternative embodiment, the cartridge identifying information encoded in each of the first and second machine readable information tags is not identical, but correspondence between the information encoded in the tags is manufactured by creating an association between the different cartridge identifying information, for example, in a relational database. Thus, proper correspondence between the cartridge identifying information scanned from the first and second machine-readable information tags confirms that the tags are associated with the same cartridge.

The cartridge 10 may further include a machine-readable sample identification tag 22 placed on the cartridge, for example on an exterior surface of the substrate 12. In one embodiment, the machine-readable sample identification tag 22 is an optically readable symbol, such a one-dimensional barcode (as shown) or a two-dimensional barcode. In other embodiments, the machine-readable sample identification tag is an electronically readable tag, such as an RFID chip or an EEPROM chip, embedded within the substrate 12.

The machine-readable sample identification tag is encoded with information identifying the nature and/or source of the sample material that is to be processed in the sample processing cartridge 10. Alternatively, the machine-readable sample identification tag is encoded with information that enables a table lookup of information identifying the nature and/or source of the sample material that is to be processed. In an embodiment, the machine-readable sample identification tag is encoded with information identifying a patient from whom the sample to be processed was obtained or is encoded with information that facilitates a database retrieval of information identifying the patient. Other information that may be encoded in the sample identification tag—or retrievable based on information encoded in the sample identification tag—may include the date on which the sample was acquired and the test(s) that is(are) to be performed on the sample. In various embodiments, the machine-readable sample identification tag may be encoded with a patient accession number uniquely associated with the patient or some other number that is associated with the patient accession number.

In one embodiment, the first machine-readable information tag 18 is configured to be read by a tag reading device located outside of the processing instrument in which the sample processing cartridge 10 is to be processed. As noted, the first machine-readable information tag 18 may comprise an optically readable tag, such as a one-dimensional or two-dimensional barcode, that can be read by a barcode scanner located outside of the processing instrument.

The second machine-readable information tag is configured to be read by a tag reading device inside the processing instrument in which the sample processing cartridge 10 will be processed. In an embodiment, the second machine-readable information tag 20 is an electronically readable tag such as an RFID tag or and EEPROM chip.

In certain embodiments, it may be preferable that the first and second machine-readable information tags are different types of tags so that a device used for reading one of the tags cannot also be used to read the other tag. For example, it may be preferable that the first machine-readable information tag is an optically readable tag, such as a barcode, that can be read outside of the processing instrument using a fixed or hand-held barcode scanner or reader and that the second machine readable information tag is not an optically readable tag, so that the second machine-readable information tag is not mistakenly read outside of the processing instrument instead of or in addition to reading the first machine-readable information tag. Thus, for example, the second machine-readable information tag may comprise an electronically readable tag such as an RFID tag or an EEPROM chip that cannot be read by a barcode scanner intended to scan the optically readable first machine-readable information tag.

Figure 3:
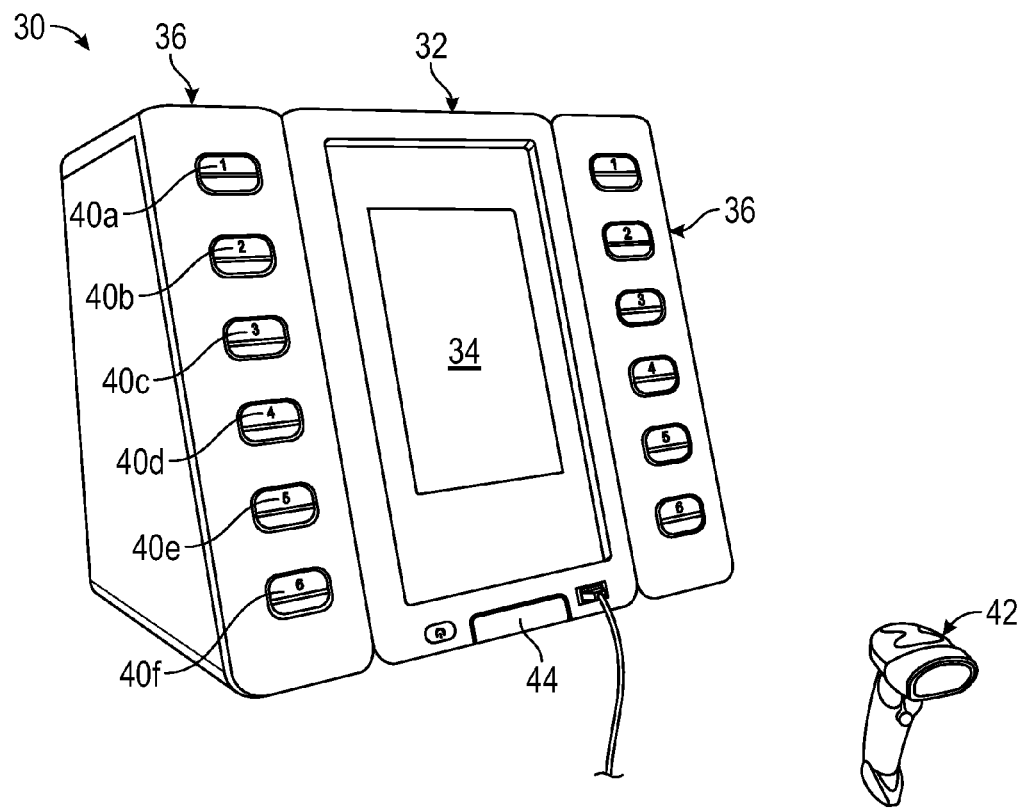
FIG. 3 is an instrument suitable for processing the cartridge.

An exemplary instrument configured for processing the sample process cartridge 10 is indicated by reference number 30 in FIG. 3. The instrument 10 comprises a control console or base 32 having an interface screen 34, one or more processing modules 36 operatively coupled to the control console 32, processing bays 40a, 40b, 40c, 40d, 40e, 40f within each processing module 36, each of which is configured to receive a sample process cartridge 10 and process the cartridge 10 independently of the other bays, and instrument software (ISW). In various embodiments, the instrument comprises one control console 32 and one or more processing modules 36, with each processing module including six processing bays 40a-40f. Each processing module 36 is operatively coupled to the control console 32, e.g., to exchange power, input and output data, and control signal transmissions with the control console 32 and may be physically connected to the control console 32 as well. The processing module(s) 34 may be an integral part of or releasably attached to the control console 32. Each processing bay 40a-40f within the processing module 36 is configured to accept one sample process cartridge 10 at a time and to process the cartridge independently of other processing bays processing other cartridges.

The ISW provides the graphical user interface via the interface screen 34 for the user to start runs, receive results, and provide inputs that at least partially control operation of the instrument 30. In various embodiments, the ISW is configured to run on a Windows® computer, and interface screen 34 comprises a touchscreen providing the primary functionality for user input. In various embodiments, the instrument 32 is configured to provide connectivity to a local area network ("LAN") and a laboratory information system ("LIS").

Each processing bay 40a-40f includes hardware, firmware, and electronics for performing a process, e.g., a molecular diagnostic assay, on a sample process cartridge 10. Each processing bay 40a-40f may include the electronics and firmware of the processing bay (such as, microprocessors and firmware on the microprocessors), circuitry that supplies power, circuitry that performs sensing of reaction products on the process cartridge, circuitry that controls heaters in the processing bay that interact with the process cartridge, circuitry that measures and controls temperatures in the process cartridge, circuitry that controls motion of various moving components of the processing bay, and circuitry that controls a pump of the processing bay.

Instrument 30 may further include a first tag reading device that is configured to read the first machine-readable information tag 18 on the cartridge 10 before the cartridge is placed into the processing instrument—e.g., into one of the processing bays 40a-40f. The first tag reading device may further be configured to read a machine-readable sample identification tag 22 placed on the cartridge 10. The tag reading device may comprise an optical tag scanner. In the illustrated embodiment, the first tag reading device comprises a handheld barcode reader 42 and/or a fixed barcode reader or scanner bay 44 positioned within the instrument 30, for example within the base 32. The handheld barcode reader 42 can be used to read the two-dimensional barcode of the first machine-readable information tag 18 as well as the one-dimensional barcode of the machine-readable sample identification tag 22 before the cartridge is inserted into one of the processing base 40a-40f of the processing instrument 30. Alternatively, the barcode scanner can be provided within a scanner bay 44 into which the cartridge may be inserted to scan barcodes 18 and 22 before removing the cartridge 10 from the scanner bay 44 and inserting the cartridge 10 into one of the processing bays 40a-40f.

Figure 4:
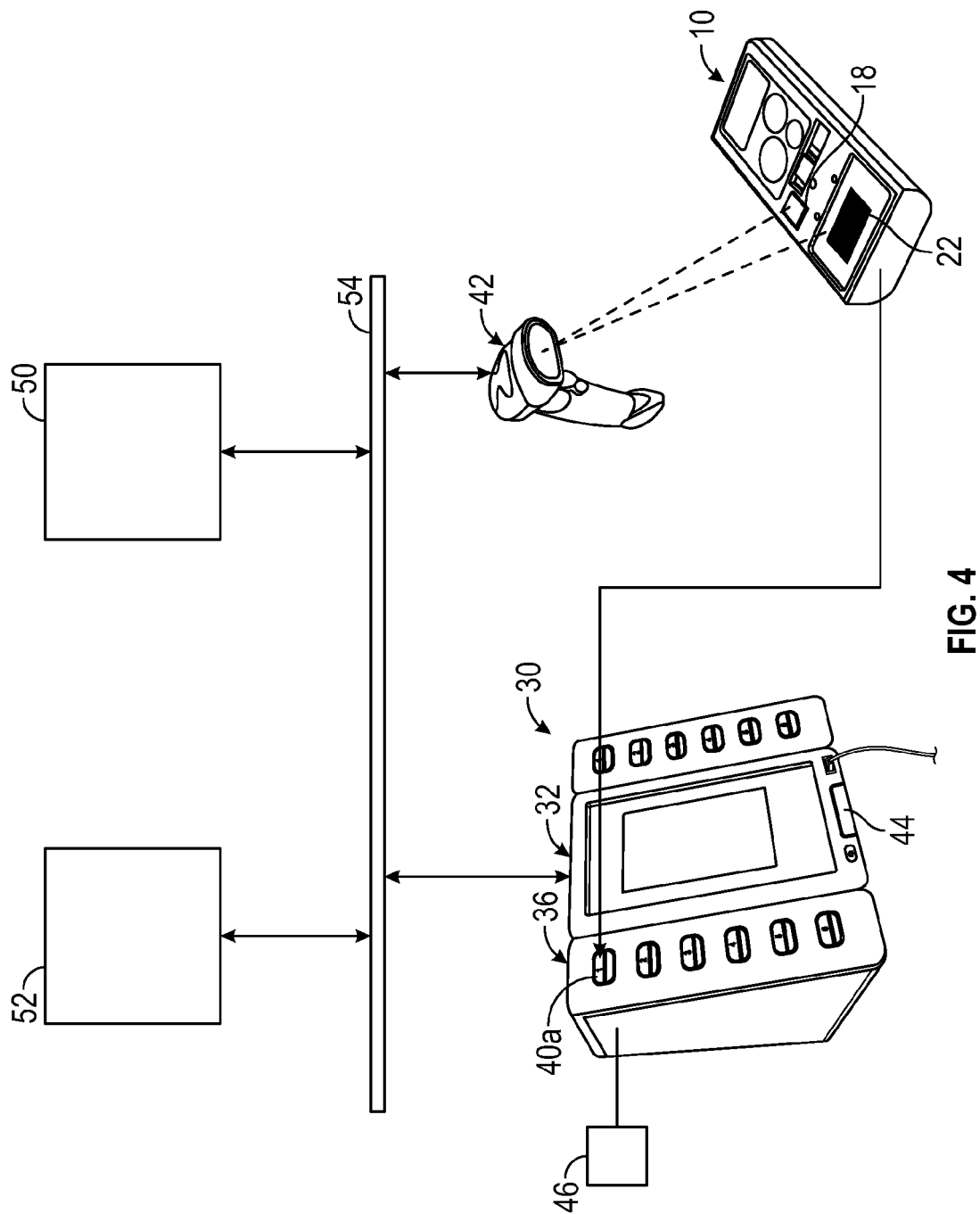
FIG. 4 is a schematic view of a data processing system for processing redundant identification data associated with the sample processing cartridge.

A data processing system for processing redundant identification data associated with the cartridge 10 is schematically shown in FIG. 4. Various components of the system, such as the processing instrument 30 and a first tag reading device, which may comprise the handheld barcode scanner 42 and/or an instrument-mounted scanner bay 44, are connected via a laboratory information system (LIS) or other wired or wireless network represented by reference number 54 in FIG. 4 to data processing assets such as a first data processor element 50 and a second data processor element 52. The processor elements 50 and 52 may comprise different parts of a common processor, e.g., a computer, or different elements of a common data processing algorithm that is executed by the processing assets of the system.

In general, aspects of the disclosure are implemented via control and computing hardware components, user-created software, data input components, and data output components. Hardware components, e.g., processor elements 50, 52, include computing and control modules (e.g., system controller(s)), such as microprocessors and computers, configured to effect computational and/or control steps by receiving one or more input values, executing one or more algorithm steps stored on non-transitory machine-readable media (e.g., software) that provide instruction for manipulating or otherwise acting on the input values, and output one or more output values. Such outputs may be displayed or otherwise indicated to a user for providing information to the user, for example information as to the status of the instrument or a process being performed thereby, or such outputs may comprise inputs to other processes and/or control algorithms. Data input components comprise elements by which data is input for use by the control and computing hardware components. Such data inputs may comprise positions sensors, motor encoders, as well as manual input elements, such as graphic user interfaces, keyboards, touch screens, microphones, switches, manually-operated scanners, voice-activated input, etc. Data output components may comprise hard drives or other storage media, graphic user interfaces, monitors, printers, indicator lights, or audible signal elements (e.g., buzzer, horn, bell, etc.).

Software comprises instructions stored on non-transitory computer-readable media which, when executed by the control and computing hardware, cause the control and computing hardware to perform one or more automated or semi-automated processes.

In a typical implementation, before the cartridge 10 is placed into the processing instrument 30, the first machine-readable information tag 18 is read by the first tag reading device, e.g., barcode reader 42 or 44, and the machine-readable sample identification tag 22 is also read by the first tag reading device, e.g. handheld barcode reader 42 or 44. Data scanned from the machine-readable tags 18 and 22 is communicated directly or indirectly by the network 54 to the first data processor element 50. First data processor element 50 is configured, e.g. programmed, to associate information read by the tag reading device 42 from the first machine-readable information tag 18 with information read by the tag reading device 42 from the machine-readable sample identification tag 22. This will create an association between information uniquely identifying the cartridge 10 that is encoded in the first machine-readable information tag 18 with information uniquely identifying the sample (e.g., patient accession number) that is encoded in the machine readable sample identification tag 22.

In one embodiment, the instrument 30 will instruct the user to enter identifying information for a particular bay 40a-40f into which the cartridge is to be inserted after sample has been added to the cartridge. Thus, the information scanned from the first machine-readable information tag 18 and the machine-readable sample identification tag 22 becomes associated with the particular processing bay, e.g., 40a.

Cartridge 10 is then placed into the processing instrument 30, for example, into processing bay 40a. After the cartridge 10 is placed into the instrument 30, a second tag reading device operatively associated with the processing instrument and indicated by box 46 in FIG. 4 is configured to read the second machine-readable information tag 20. Second tag reading device 46 may comprise an optical tag scanner, e.g., a bar code scanner, or an electronic tag reading device (scanner)—which may be configured to scan by wireless or contactless transmission or by electrical contact with some portion of the second machine readable information tag 20. Data read by the second tag reading device 46 is communicated via the network 54 to the second data processor element 52, which is configured, e.g., programmed, to compare the information read by the second tag reading device 46 from the second machine-readable information tag 20 with the information read by the first tag reading device 42 from the first machine readable information tag 18 to ensure that the cartridge identifying information encoded into the first machine-readable information tag 18 corresponds to the cartridge identifying information encoded into the second machine-readable information tag 20.

In one embodiment, where the cartridge identifying information encoded into the first and second machine-readable information tags 18 and 20 comprises identical serial numbers, the second data processor 52 confirms that the information read from the first and second machine-readable information tags is identical. In another embodiment, where the information encoded into the first and second machine-readable information tags is not identical but is associated with each other in a relational data base, the second data processor element 52 will be configured to do a table look-up to confirm that the cartridge identifying information read from the second machine-readable information tag 20 is properly associated with the cartridge identifying information that was read from the first machine-readable information tag 18.

Figure 5:
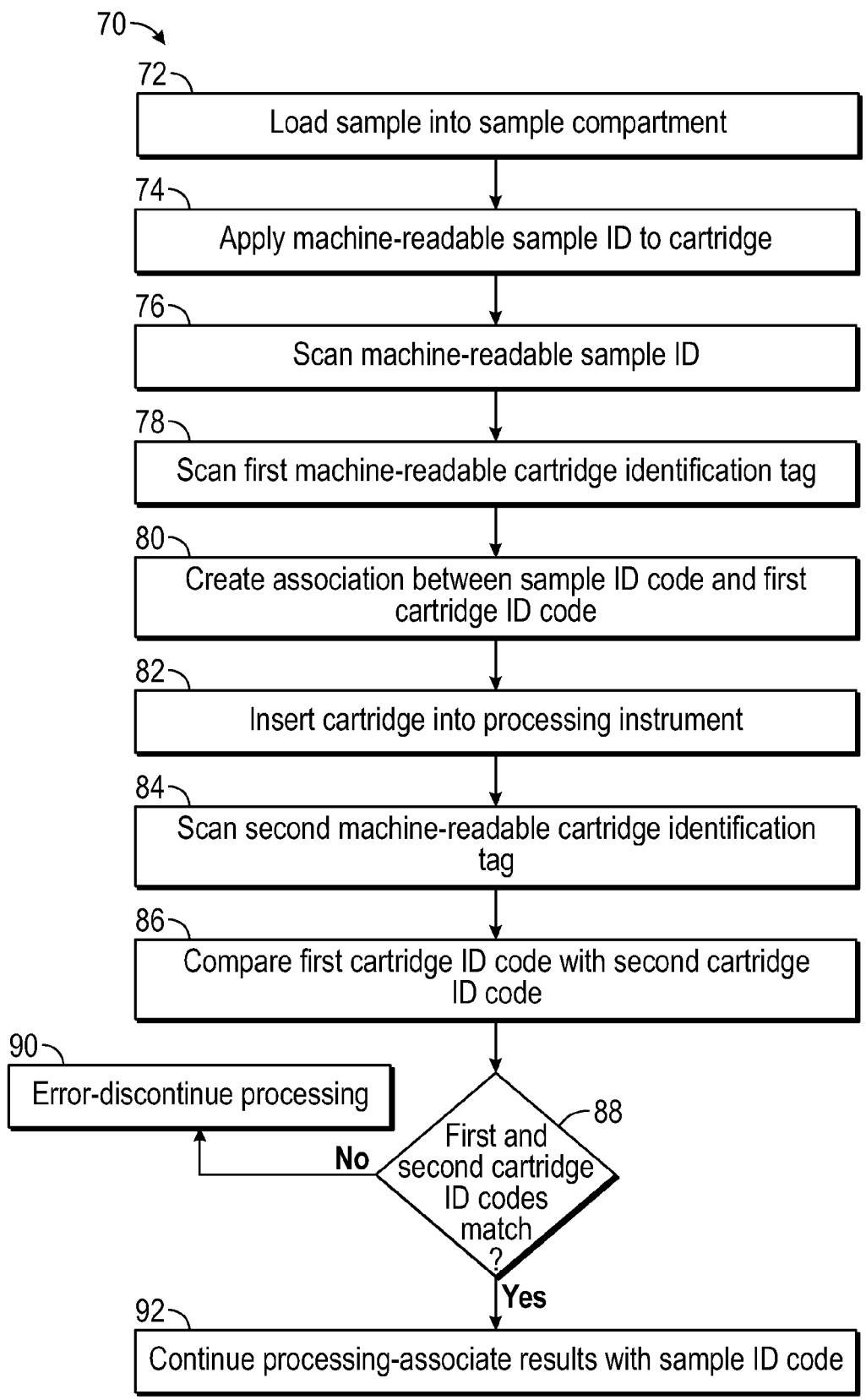
FIG. 5 is a flow chart illustrating a redundant identification process using the sample cartridge.

FIG. 5 is a flow chart illustrating a redundant identification process 70 using a sample processing device, such as sample cartridge 10, and a sample processing instrument that receives the device, such as instrument 30.

In a first step 72, sample is placed into the sample compartment 14 of the sample processing cartridge 10, and then the compartment is sealed, e.g., by closing a cap over a sample well.

In step 74, a machine-readable sample identification tag 22 is placed on the sample processing cartridge 10. The machine-readable sample identification tag 22 may be an adhesively-backed label that is provided with the sample material to be applied to the cartridge at the time that sample material is placed in the sample compartment 14 and may include a patient accession number or other sample-identifying information. In another embodiment, the machine-readable sample identification tag may comprises a tag, such as a bar code, an RFID chip, or a EEPROM chip, that is pre-applied to the sample processing cartridge, e.g., by the manufacturer, and which is encoded with a code that is unique to that sample processing cartridge. The user then scans the pre-applied machine-readable sample identification tag to enter the unique code into the instrument control system and then enters sample identification information to associate the sample identification information with the unique code.

In steps 76 and 78, the user scans the machine-readable sample identification 22 and the first machine-readable information tag 18 with the first tag reading device 42 (the order of steps 76 and 78 may be reversed). In step 80, the first data processor element 50 creates an association between the sample identification information scanned from the sample identification tag 22 and the cartridge identification information scanned from the first machine-readable information tag 18.

In step 82, the cartridge 10 is inserted into a sample processing bay 40a-40f of the sample processing instrument 30.

In step 84, with the cartridge 10 disposed within the sample processing instrument 30, the second tag reading device 46 reads the second machine-readable information tag 20. Step 84 may be triggered by a switch that is tripped when the cartridge is inserted into the sample processing instrument 30.

In step 86, the second data processor element 52 compares the information scanned by the second tag reading device 46 from the second machine-readable information tag 20 with the information scanned by the first tag reading device 42/44 from the first machine-readable information tag 18. In step 88, the second data processor element 52 determine whether the identifying information scanned from the second machine-readable information tag 20 properly corresponds to the identifying information scanned from the first machine-readable information tag 18.

If the identifying information scanned from the second machine-readable information tag 20 does not properly correspond to the identifying information scanned from the first machine-readable information tag 18, the cartridge 10 is rejected and the processing instrument 30 ceases processing of the cartridge (step 90). A visual and/or audible warning signal may be provided by the instrument 30, and the instrument may include an eject feature for ejecting the cartridge from the instrument—e.g., from the processing bay 40a. If the identifying information scanned from the second machine-readable information tag 20 properly corresponds to the identifying information scanned from the first machine-readable information tag 18, the processing instrument 30 continues operation, and test results may be associated with the sample-identifying information scanned by the first tag-reading device from the machine-readable sample identification tag 22 (step 92).

EXEMPLARY EMBODIMENTS

The following embodiments are encompassed by the foregoing disclosure.

Embodiment 1

A sample processing cartridge comprising:
- a substrate configured to be inserted into a sample processing instrument;
- a sample compartment supported on said substrate and configured to contain a fluid sample material;
- one or more process compartments supported on said substrate and configured to contain a process material, wherein said sample compartment is connected or connectable to at least one process compartment;
- a first machine-readable information tag mounted on or embedded in said substrate and encoded with cartridge-identifying information and configured to be read by a device that is external to a sample processing instrument; and
- a second machine-readable information tag mounted on or embedded in said substrate and encoded with cartridge-identifying information corresponding to the cartridge-identifying information encoded in said first machine-readable information tag and configured to be read by a device within a sample processing instrument.

Embodiment 2

The sample processing cartridge of embodiment 1, wherein said first machine-readable information tag comprises an optically-readable tag.

Embodiment 3

The sample processing cartridge of embodiment 1 or embodiment 2, wherein said first machine-readable information tag comprises a bar code.

Embodiment 4

The sample processing cartridge of any one of embodiments 1 to 3, wherein said first machine readable information tag comprises a 1-D or a 2-D bar code.

Embodiment 5

The sample processing cartridge of any one of embodiments 1 to 4, wherein said second machine-readable information tag comprises an electronically-readable tag.

Embodiment 6

The sample processing cartridge of any one of embodiments 1 to 5, wherein said second machine-readable information tag comprises a wirelessly-readable tag.

Embodiment 7

The sample processing cartridge of any one of embodiments 1 to 5, wherein said second machine-readable information tag comprises an RFID tag or an EEPROM tag.

Embodiment 8

The sample processing cartridge of any one of embodiments 1 to 7, wherein the cartridge-identifying information encoded in said second machine-readable information tag comprises information that is identical to the cartridge-identifying information encoded in said first machine-readable information tag.

Embodiment 9

The sample processing cartridge of any one of embodiments 1 to 8, wherein cartridge-identifying information comprises an identification code comprised of a unique combination of numeric and/or alphabetic characters.

Embodiment 10

The sample processing cartridge of any one of embodiments 1 to 9, further comprising a machine-readable sample identification tag encoded with sample-identifying information and configured to be read by a device that is external to a sample processing instrument.

Embodiment 11

A system for processing a sample comprising:
A. a sample processing cartridge comprising:
(1) a substrate;
(2) a sample compartment supported on said substrate and configured to contain a fluid sample material;

(3) one or more process compartments supported on said substrate and configured to contain a process material, wherein said sample compartment is connected or connectable to at least one process compartment;
(4) a first machine-readable information tag mounted on or embedded in said substrate and encoded with cartridge-identifying information and configured to be read by a device that is external to a sample processing instrument; and
(5) a second machine-readable information tag mounted on or embedded in said substrate and encoded with cartridge-identifying information corresponding to the cartridge-identifying information encoded in said first machine-readable information tag;
B. a first tag reading device configured to read said first machine-readable information tag and to read a machine-readable sample identification tag placed on said cartridge;
C. a first data processor element configured to associate information read from said first machine-readable information tag by said first tag reading device with information read from said machine-readable sample identification tag by said first tag reading device;
D. a processing instrument configured to receive said sample processing cartridge;
E. a second tag reading device operatively associated with the processing instrument and configured to read said second machine-readable information tag when a sample processing cartridge is placed in the processing instrument; and
F. a second data processor element configured to compare the information read from said second machine-readable information tag by said second tag reading device with information read from said first machine-readable information tag by said first tag reading device to ensure the cartridge-identifying information contained in said first machine-readable information tag corresponds to the cartridge-identifying information contained in said second machine-readable information tag.

Embodiment 12

The system of embodiment 11, wherein said second data processing element is further configured to enable operation of said processing instrument if the cartridge-identifying information contained in said first machine-readable information tag corresponds to the cartridge-identifying information contained in said second machine-readable information tag or disable operation of said processing instrument if the cartridge-identifying information contained in said first machine-readable information tag does not correspond to the cartridge-identifying information contained in said second machine-readable information tag.

Embodiment 13

The system of embodiment 11 or embodiment 12, wherein said first machine-readable information tag comprises an optically-readable tag, and said first tag reading device comprises an optical tag scanner.

Embodiment 14

The system of any one of embodiments 11 to 13, wherein said first machine-readable information tag comprises a bar code, and said first tag reading device comprises a hand-held bar-code scanner.

Embodiment 15

The system of any one of embodiments 11 to 14, wherein said first machine readable information tag comprises a 1-D or a 2-D bar code.

Embodiment 16

The system of any one of embodiments 11 to 15, wherein said second machine-readable information tag comprises an electronically-readable tag, and said second tag reading device comprises an electronic tag reading device.

Embodiment 17

The system of any one of embodiments 11 to 16, wherein said second machine-readable information tag comprises a wirelessly-readable tag, and said second tag reading device comprises a wireless tag scanner.

Embodiment 18

The system of any one of embodiments 11 to 17, wherein said second machine-readable information tag comprises an RFID tag or an EEPROM tag.

Embodiment 19

The system of any one of embodiments 11 to 18, wherein the cartridge-identifying information encoded in said second machine-readable information tag comprises information that is identical to the cartridge-identifying information encoded in said first machine-readable information tag.

Embodiment 20

The system of any one of embodiments 11 to 19, wherein cartridge-identifying information comprises an identification code comprised of a unique combination of numeric and/or alphabetic characters While the subject matter of this disclosure has been described and shown in considerable detail with reference to certain illustrative embodiments, including various combinations and sub-combinations of features, those skilled in the art will readily appreciate other embodiments and variations and modifications thereof as encompassed within the scope of the present invention. Moreover, the descriptions of such embodiments, combinations, and sub-combinations is not intended to convey that the inventions requires features or combinations of features other than those expressly recited in the claims. Accordingly, the scope of this disclosure is intended to include all modifications and variations encompassed within the spirit and scope of the following appended claims.

The invention claimed is:
1. A system for processing a sample comprising:
A. a sample processing cartridge comprising:
(1) a substrate;
(2) a sample compartment supported on said substrate and configured to contain a fluid sample material;
(3) one or more process compartments supported on said substrate and configured to contain a process material, wherein said sample compartment is connected or connectable to at least one process compartment;
(4) a first machine-readable information tag mounted on or embedded in said substrate and encoded with cartridge-identifying information and configured to be read by a device that is external to a sample processing instrument;
  (5) a second machine-readable information tag mounted on or embedded in said substrate and encoded with cartridge-identifying information corresponding to the cartridge-identifying information encoded in said first machine-readable information tag; and
  (6) a machine-readable sample identification tag disposed on said substrate;
B. a first tag reading device configured to read said first machine-readable information tag and to read said machine-readable sample identification;
C. a first data processor element configured to associate information read from said first machine-readable information tag by said first tag reading device with information read from said machine-readable sample identification tag by said first tag reading device;
D. a processing instrument configured to receive said sample processing cartridge;
E. a second tag reading device operatively associated with the processing instrument and configured to read said second machine-readable information tag when a sample processing cartridge is placed in the processing instrument; and
F. a second data processor element that is in direct or indirect communication with each of the first tag reading device and the second tag reading device, wherein the second data processor element is configured to compare the information read from said second machine-readable information tag by said second tag reading device with information read from said first machine-readable information tag by said first tag reading device to ensure the cartridge-identifying information contained in said first machine-readable information tag corresponds to the cartridge-identifying information contained in said second machine-readable information tag.

2. The system of claim 1, wherein said second data processing element is further configured to enable operation of said processing instrument if the cartridge-identifying information contained in said first machine-readable information tag corresponds to the cartridge-identifying information contained in said second machine-readable information tag or disable operation of said processing instrument if the cartridge-identifying information contained in said first machine-readable information tag does not correspond to the cartridge-identifying information contained in said second machine-readable information tag.

3. The system of claim 1, wherein said first machine-readable information tag comprises an optically-readable tag, and said first tag reading device comprises an optical tag scanner.

4. The system of claim 1, wherein said first machine-readable information tag comprises a bar code, and said first tag reading device comprises a hand-held bar-code scanner.

5. The system of claim 1, wherein said first machine readable information tag comprises a 1-D or a 2-D bar code.

6. The system of claim 1, wherein said second machine-readable information tag comprises an electronically-readable tag, and said second tag reading device comprises an electronic tag reading device.

7. The system of claim 1, wherein said second machine-readable information tag comprises a wirelessly-readable tag, and said second tag reading device comprises a wireless tag scanner.

8. The system of claim 1, wherein said second machine-readable information tag comprises an RFID tag or an EEPROM tag.

9. The system of claim 1, wherein the cartridge-identifying information encoded in said second machine-readable information tag comprises information that is identical to the cartridge-identifying information encoded in said first machine-readable information tag.

10. The system of claim 1, wherein cartridge-identifying information comprises an identification code comprised of a unique combination of numeric and/or alphabetic characters.

* * * * *